US00PP19826P3

(12) United States Plant Patent
Davidson et al.

(10) Patent No.: US PP19,826 P3
(45) Date of Patent: Mar. 17, 2009

(54) APPLE TREE NAMED 'LADY LAURA'

(50) Latin Name: *Malus domestica*
Varietal Denomination: Lady Laura

(76) Inventors: Max Davidson, c/o Fleming's Nurseries, Fleming Lane, Monbulk, Victoria (AU), 3793; Grahame Davidson, c/o Fleming's Nurseries, Fleming Lane, Monbulk, Victoria (AU), 3793

( * ) Notice: Subject to any disclaimer, the term of this patent is extended or adjusted under 35 U.S.C. 154(b) by 0 days.

(21) Appl. No.: 11/493,500

(22) Filed: Jul. 25, 2006

(65) Prior Publication Data

US 2008/0184402 P1 Jul. 31, 2008

(51) Int. Cl.
*A01H 5/00* (2006.01)

(52) U.S. Cl. ..... Plt./161
(58) Field of Classification Search ..... Plt./161
See application file for complete search history.

*Primary Examiner*—Annette H Para
*Assistant Examiner*—Louanne C Krawczewicz Myers
(74) *Attorney, Agent, or Firm*—Klarquist Sparkman, LLP

(57) ABSTRACT

A new apple variety distinguished by the amount and intensity of over-color of the fruit and the earlier coloration of the fruit.

3 Drawing Sheets

Latin name of the genus and species of the plant claimed: *Malus domestica.*
Variety denomination: 'Lady Laura'.

BACKGROUND OF THE INVENTION

The present invention relates to a new and distinct variety of apple tree named 'Lady Laura.' The new tree resulted from a spontaneous limb sport mutation of 'Cripps Pink' (U.S. Plant Pat. No. 7,880). The 'Cripps Pink' tree containing the limb sport of the new variety was discovered growing in a cultivated area in Borenore NSW, Australia.

BRIEF SUMMARY OF THE INVENTION

The 'Lady Laura' variety is distinguished from other apple varieties due to the following unique combination of characteristics: the amount and intensity of over color of the fruit, and the earlier coloration of fruit in comparison to 'Cripps Pink'.

Asexual reproduction of this new variety by budding and grafting shows that the foregoing characteristics come true to form, are firmly fixed, and are established and transmitted through succeeding propagations. The initial asexual reproduction of the new cultivar was performed in New South Wales, Australia.

Certain characteristics of this variety, such as growth and color, may change with changing environmental conditions (such as light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart.

Figure 1:
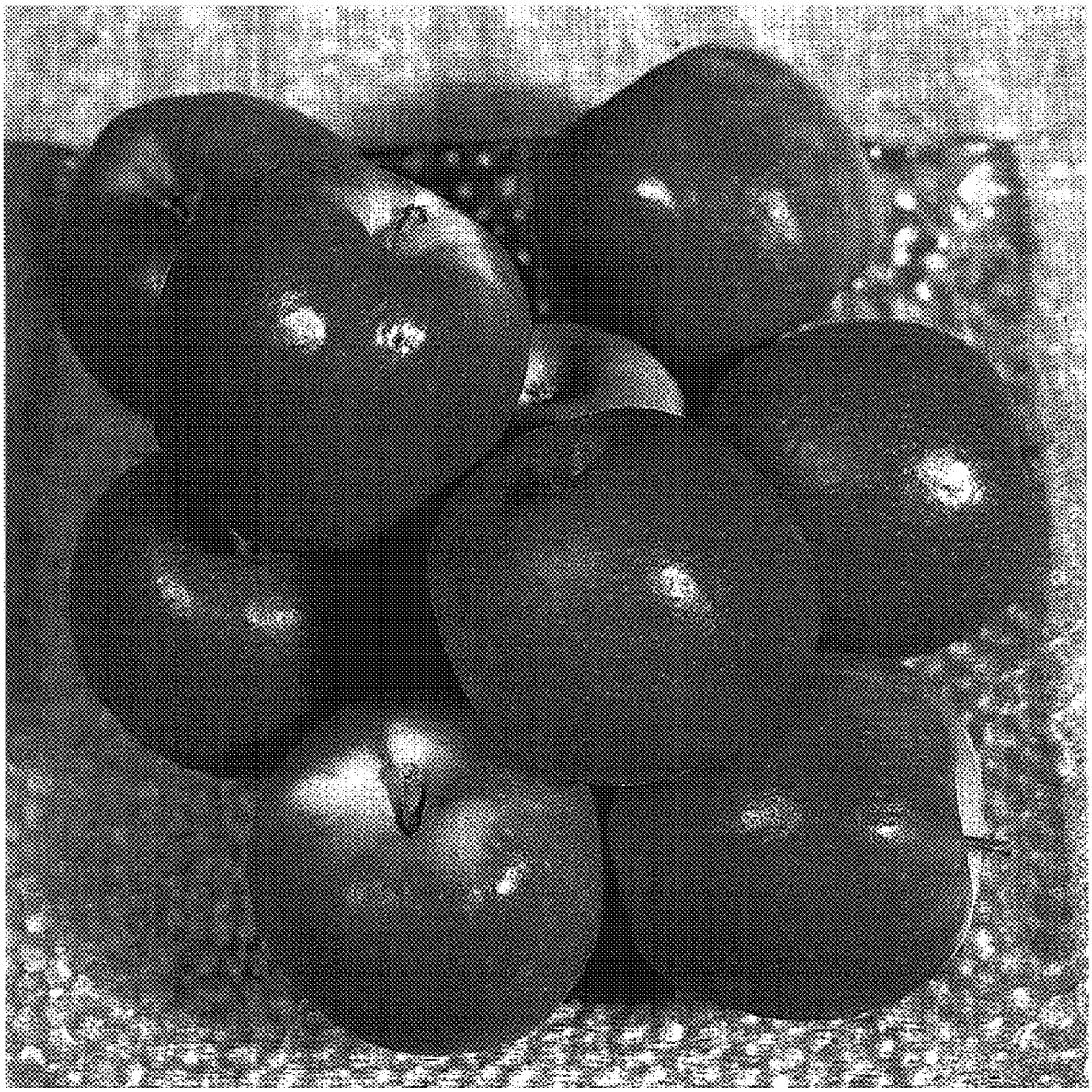
FIG. 1 is a photograph showing typical fruit of the new variety.
Figure 2:
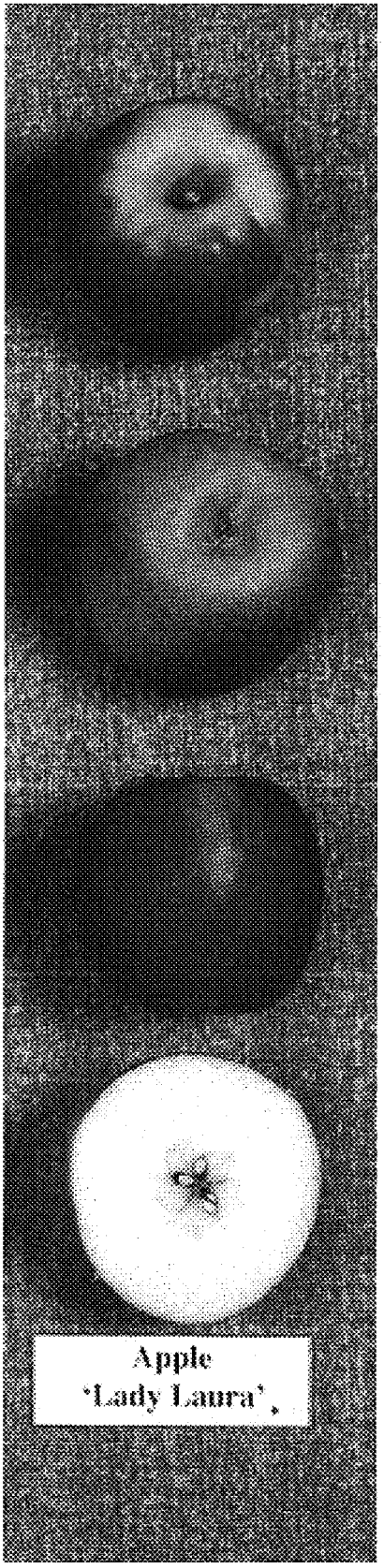
FIG. 2 is a photograph showing typical fruit of the new variety as well as the fruit cut in half.

The accompanying color photographs shows typical specimens of the fruit and leaves of this new apple tree variety and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photograph alone.

DETAILED DESCRIPTION

BOTANICAL

The following detailed description of the 'Lady Laura' variety is based on observations of the original limb sport and asexually reproduced progeny. The observed progeny are trees which were four years of age and growing on Exemla 9 rootstock (unpatented) in Taggerty, Victoria, Australia.

Scientific Name: *Malus domestica* 'Lady Laura'.
Parentage: Spontaneous limb sport mutation of 'Cripps Pink'.
Tree:
- *Vigor.*—Medium.
- *Overall shape.*—Upright.
- *Height.*—About 5 to 6 feet.
- *Width.*—Overall spread of about 4 feet.
- *Caliper.*—Approximately 3 cm in diameter when measured from approximately 55 cm above the ground.
- *Trunk.*—Medium stocky.
- *Trunk bark texture.*—Medium rough with lenticels.
- *Trunk bark color.*—Grey/Green/Cream (RHS 195B).
- *Patches or other markings.*—Lenticels approximately 5 per square centimeter. Measuring approximately 4 mm long and 1 mm wide, very narrow elliptic in shape.

*Primary branches.*—Upright habit. Measuring in length between 56 cm and 28 cm when measured approximately 55 cm above the crotch of the tree. Measuring approximately 1 cm in diameter.

*Branch color.*—One-year old branches are green (RHS 144B) in color, while two-year old branches are green-brown (RHS 199B) in color.

*Branch pubescence.*—Present.

*Branch lenticels.*—Medium density, approximately 38 per square inch; greyed-orange (RHS 164D) in color.

*Internodes.*—Average internode length is about one and one-sixteenth inch on a one-year old shoot.

*Bearing.*—Annual. No particular disease resistance or susceptibility observed.

Leaves:

*Texture.*—Medium thick. Approximately 1 mm thick

*Sheen.*—Medium dull.

*Length.*—About 3½ inches to about 5 inches, averaging about 4¼ inches.

*Width.*—About 2¼ inches to about 2¾ inches, averaging about 2½ inches.

*Petiole.*—About 1 and one-eighth inches long; red-green in color (red RHS 179A and green 148D); about one-sixteenth inch in diameter. Average 2 stipules per petiole measuring between 10–14 mm in length and 3 mm in width. Color is medium green (RHS 137A). Each stipule shows a slight serration of the margin. The stipules have a cuneate base and a pointed sub-acute apex.

*Margin.*—Irregularly serrated.

*Tip shape.*—Acutely pointed.

Figure 3:
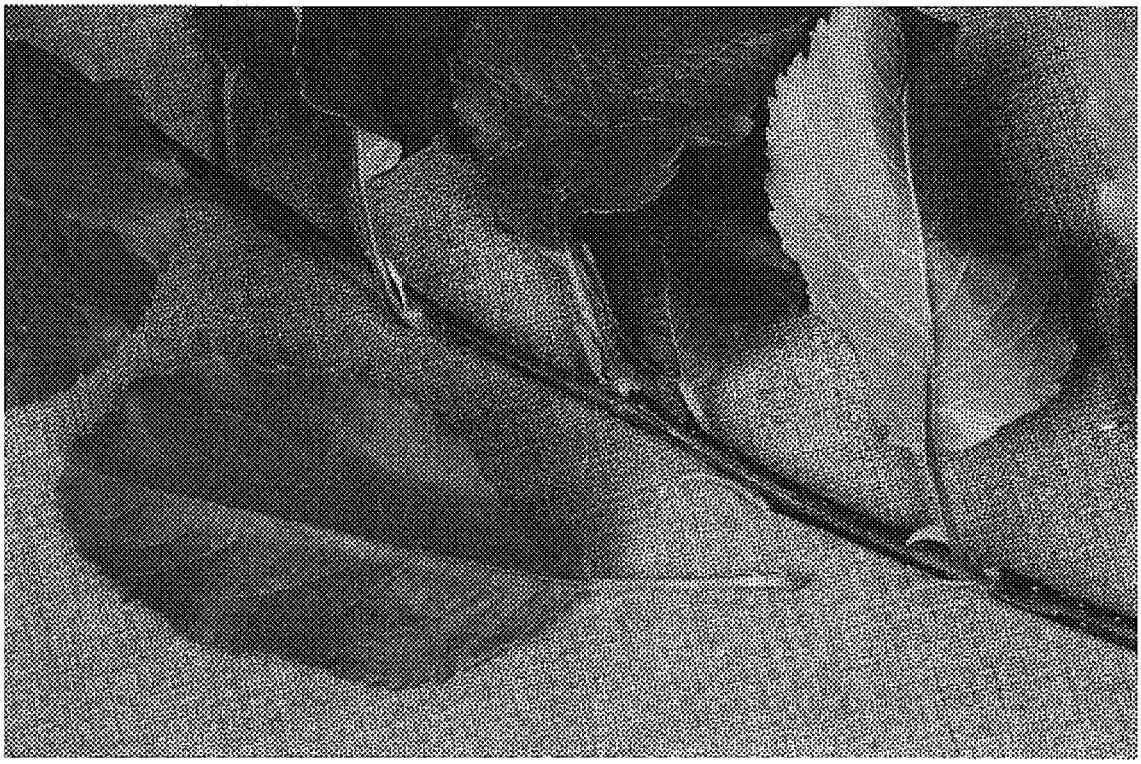
FIG. 3 is a photograph showing typical leaves of the new variety.

*Venation.*—Lateral veins are palmate appearance but the smaller intersecting veins are reticulate (FIG. 3).

*Base of the leaf.*—Between cuneate to rounded.

*Leaf color.*—Upper leaf surface: Green (RHS 137A). Lower leaf surface: Light green (RHS 147B). Vein: Light green (RHS 147C).

*Pubescence.*—Yes. The length, width, thickness and other measurements were obtained from observations of ten typical leaves in late spring.

Flowers:

*Size.*—Medium size, typical flower measuring about 30 mm across.

*Color.*—Unopened bud: Pink (RHS 67B). At time of observation there were small buds measuring 6 mm in diameter and 9 mm long. These buds still remained tight and ranged in color from light pink (RHS 61D) to darker pink (RHS 63A). Also observed were larger swollen buds measured 12 mm in diameter and 19 mm long. Opened flower/petals: Open flowers of the new cultivar are rounded at the apex of the petal and slightly pointed where the individual petals meet at the base. The upper margin of the petal displays a light pink coloration similar to RHS 65D which then pales to white, RHS 155D, across the mid and lower surfaces of petal. Petals round to ovate measuring approximately 10–15 mm in diameter. Moderate pollen (yellow in color, RHS 6D).

*Petals.*—5 petals per flower; round to ovate in shape; about five-eighths (to slightly larger) inch long.

*Stamen.*—16 stamens, each about 9 mm long and cream white (RHS 155D) in color.

*Anthers.*—Pale yellow (RHS 6D) in color.

*Pistil.*—Stigma is about 8 mm long; 5 styles, fused at base, and pale brown (RHS 162D) in color.

*Sepals.*—About 6 mm in length and about 3 mm wide; recurved shape; both the upper and lower surfaces are light green (RHS 142D) in color; pubescence present and each flower has 5 sepals.

*Fragrance.*—Light.

*Bloom season.*—Early to mid-full bloom observed. Timing varies depending on chill units.

Fruit: (Observations from a limited number of typical fruit in April 2005).

*Size.*—About 2 and seven-eighths inches long and 3 inches wide.

*Form.*—Round oblong.

*Cavity.*—Medium broad to deep. Stem cavity measures approximately 18 mm–20 mm wide and 16 mm–18 mm deep.

*Basin.*—About seven-sixteenths inch deep and about seven-eighths inch wide; pubescence present. From the fruit observed, the eye is sometimes partially open or closed but does not favor either and the basin is rounded in shape.

*Stem.*—About five-eighths inch long and one-eighth inch in diameter; yellow green (RHS 152D) in color.

*Locules.*—Mostly closed locules.

*Skin.*—Medium thick. The fruit can develop a waxy feel if over mature but no cracking has been evident.

*Lenticels.*—Prominent. The small roundish lenticels appear at 6 or more per square centimeter. Each lenticel measures approximately 1 mm–2 mm in diameter. Lenticels are round in appearance and are cream white in color (RHS 158 C).

*Locules.*—There are five, which are approximately 3 mm across the base and meet together at the apex, which is pointed.

*Color.*—General color effect: Solid dark pink-red (RHS 47A and 50A) over yellowish ground color (RHS 10B). The fruit of the new cultivar displays an attractive general color that incorporates bright red similar to that of both RHS 47 A and 50 A respectively. The solid blush of the fruit over color can have some variation, which could include other RHS colors from plate 47. Ground color: Varies from yellow-green (between RHS 145B and 145C) to yellow (RHS 10B). Overcolor: Dark pink to red. The fruit of the new cultivar displays an attractive general color that incorporates bright red similar to that of both RHS 47A and 50A. The solid blush of the fruit over color can have some variation, including other RHS colors from plate 47). Overcolor percentage of approximately 90% compared to 'Cripps Pink' of approximately 30–80%. The overcolor is more intense and there is a greater percentage of color and more even overcolor that 'Cripps Pink.' The fruit achieve overcolor approximately 14 days earlier than 'Cripps Pink.'Russetting: Absent.

*Fruit properties at maturity* (*based on* 10 *apples tested in April* 2005).—Firmness: About 8 kg, averaging about 8.5 kg/cm$^2$. Soluble solids: Averaging about 15%. Flavor: Mild. Juiciness: Medium. Flesh color: Creamy light yellow (RHS 4D). The flesh has a medium acid content and balanced flavour. Aroma: Mild pleasant.

*Core.*—The bundle area of the core is large and unsymmetrical. The core lines are defined, conspicuous.

*Seed.*—About 2 seeds per cell; acute shaped; about three-eighths inch long and about three-sixteenth inch wide; brown (RHS 174A) in color.

*Fruit production.*—First picking date in Victoria, Australia was about $4^{th}$ of April, and last picking date was about $10^{th}$ of April 2005.

*Storage.*—Fruit can be stored up to 4 months in cold storage (34° F.).

*Usage.*—Eating.

We claim:

1. A new and distinct variety of apple tree, substantially as herein shown and described.

* * * * *